United States Patent
Helmer

(10) Patent No.: US 10,744,272 B2
(45) Date of Patent: Aug. 18, 2020

(54) SEALED NEEDLE ASSEMBLY FOR MEDICAMENT DELIVERY DEVICE

(71) Applicant: SANOFI-AVENTIS DEUTSCHLAND GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/553,778

(22) PCT Filed: Feb. 25, 2016

(86) PCT No.: PCT/EP2016/053998
§ 371 (c)(1),
(2) Date: Aug. 25, 2017

(87) PCT Pub. No.: WO2016/135251
PCT Pub. Date: Sep. 1, 2016

(65) Prior Publication Data
US 2018/0064884 A1 Mar. 8, 2018

(30) Foreign Application Priority Data
Feb. 27, 2015 (EP) .................................... 15157002

(51) Int. Cl.
*A61M 5/32* (2006.01)
*A61M 5/162* (2006.01)
*A61M 5/24* (2006.01)

(52) U.S. Cl.
CPC ........ *A61M 5/3202* (2013.01); *A61M 5/1626* (2013.01); *A61M 5/3204* (2013.01);
(Continued)

(58) Field of Classification Search
CPC ........ A61M 2005/2462; A61M 5/1626; A61M 5/3202; A61M 5/3204; A61M 5/3213;
(Continued)

(56) References Cited

U.S. PATENT DOCUMENTS

| | | | |
|---|---|---|---|
| 4,972,843 A | 11/1990 | Broden | |
| 5,354,287 A | 10/1994 | Wacks | |

(Continued)

FOREIGN PATENT DOCUMENTS

| | | |
|---|---|---|
| JP | 2013-507216 | 3/2013 |
| JP | 2013-533096 | 8/2013 |

(Continued)

OTHER PUBLICATIONS

International Preliminary Report on Patentability in International Application No. PCT/EP2016/053998, dated Aug. 29, 2017, 7 pages.

(Continued)

*Primary Examiner* — Brandy S Lee
(74) *Attorney, Agent, or Firm* — Fish & Richardson P.C.

(57) ABSTRACT

The disclosure relates to a needle assembly adapted to couple with a medicament delivery device including a needle having a proximal tip and a distal tip, a needle hub coupled to the needle, a body adapted to engage the needle hub, a removable needle cap adapted to cover the distal tip, and a removable sealing element. The sealing element is adapted to seal an open proximal end of a compartment of the body, including the proximal tip, in such a manner that the proximal tip is housed in a sealed environment before use of the needle. The disclosure further relates to a medicament delivery device including such a needle assembly.

20 Claims, 5 Drawing Sheets

(52) U.S. Cl.
CPC ........ *A61M 5/3213* (2013.01); *A61M 5/3269*
(2013.01); *A61M 5/3216* (2013.01); *A61M
2005/2462* (2013.01)

(58) Field of Classification Search
CPC ... A61M 5/3216; A61M 5/3269; B32B 27/30;
G02B 5/30; G02F 1/1335; G02F 1/13363
See application file for complete search history.

(56) References Cited

U.S. PATENT DOCUMENTS

| | | | |
|---|---|---|---|
| 6,733,465 B1 | 5/2004 | Smutney et al. | |
| 2012/0016300 A1* | 1/2012 | Ruan | A61M 5/002 |
| | | | 604/110 |
| 2012/0277685 A1* | 11/2012 | Limaye | A61M 5/3243 |
| | | | 604/192 |

FOREIGN PATENT DOCUMENTS

| | | |
|---|---|---|
| WO | WO 93/11814 | 6/1993 |
| WO | WO 97/10014 | 3/1997 |
| WO | WO 2006/063124 | 6/2006 |
| WO | WO 2011/045386 | 4/2011 |
| WO | WO 2012/021762 | 2/2012 |
| WO | WO 2013/048310 | 4/2013 |

OTHER PUBLICATIONS

International Search Report and Written Opinion in International Application No. PCT/EP2016/053998, dated May 3, 2016, 11 pages.

* cited by examiner

SEALED NEEDLE ASSEMBLY FOR MEDICAMENT DELIVERY DEVICE

CROSS REFERENCE TO RELATED APPLICATIONS

The present application is the national stage entry of International Patent Application No. PCT/EP2016/053998, filed on Feb. 25, 2016, and claims priority to Application No. EP 15157002.5, filed in on Feb. 27, 2015, the disclosures of which are expressly incorporated herein in entirety by reference thereto.

TECHNICAL FIELD

The disclosure relates to a needle assembly and a medicament delivery device comprising such a needle assembly.

BACKGROUND

Administering an injection is a process which presents a number of risks and challenges for users and healthcare professionals, both mental and physical. Pre-filled syringes with a syringe cartridge containing a selected dosage of a medicament for administering the medicament to a patient are known in the art. The cartridges may be stored in a blistered package so that they are kept sterile until the time of use. The cartridges include a hollow injection needle that is in fluid communication with the medicament stored in the cartridge. Thus, the injection needle can be clogged after a long-term storage.

There remains a need for an improved needle assembly and an improved medicament delivery device comprising such a needle assembly.

SUMMARY

Certain aspects of the present disclosure relate to an improved needle assembly for a medicament delivery device and an improved medicament delivery device including such a needle assembly.

Exemplary embodiments of the disclosure are given in the dependent claims.

A needle assembly includes a needle having a proximal tip and a distal tip; a needle hub coupled to the needle; a body adapted to engage the needle hub and a removable needle cap adapted to cover the distal tip. Furthermore, the needle assembly includes a removable sealing element adapted to seal an open proximal end of a compartment of the body including the proximal tip in such a manner that the proximal tip is housed in a sealed environment before use of the needle.

The provided needle assembly enables a reliable sealing of the double ended needle respectively for the distal tip and the proximal tip in an initial position of the needle assembly and an uneasy unsealing at the same time. Here, the initial position describes a position of the needle assembly with a sealed needle before use of the needle. The needle assembly is engageable or engaged with a medicament delivery device including a cartridge containing a medicament. In the initial position, the proximal tip of the needle is not in contact with the medicament. Once the sealing element is removed, the proximal tip is ready for piercing the cartridge. Thus, the needle will remain sterile and clean until the beginning of an injection process.

In an exemplary embodiment, the sealing element is coupled to the needle cap such that the sealing element is removable from the compartment when the needle cap is removed from the distal tip. This provides an easy priming of the needle assembly due to removing the needle cap and the sealing element at the same time.

In an exemplary embodiment, the sealing element includes two sections, wherein one section is coupled to the compartment and the other section is coupled to the needle cap. The sections may be arranged perpendicular at least time limited, in particular when the needle assembly is in the initial position.

In a further exemplary embodiment, the one section coupled to the compartment is folded such that the proximal tip is covered by two layers of the sealing element. This enables an increased sealing of the compartment and thus of the proximal tip of the needle.

Furthermore, the other section coupled to the needle cap is arranged outside the body and extending parallel to a longitudinal axis of the needle assembly in a distal direction, whereby the distal direction is directed to a patient's site.

Expediently, the sealing element is guidable out of the body through at least one opening of the body when the needle cap is removed from the distal tip of the needle. The opening may have dimensions that correspond with dimensions of the sealing element. Otherwise, the opening may be designed as an opened section of the body having dimensions larger than the sealing element. Furthermore, the proximal needle tip may be sealed immediately before starting an injection process without risking a contamination of the proximal needle tip, e.g., by opening the needle assembly or exposing the proximal needle tip in an external environment.

In an exemplary embodiment, the at least one opening is arranged on a lateral surface of the body.

In an alternative embodiment, the at least one opening is arranged on a distal surface of the body.

In an exemplary embodiment, the sealing element includes a flexible foil. The flexible foil may be made from a plastic material enabling a reliable sealing and due to the flexible design an easy removal with less friction.

The connection of the sealing element and the body may be realized by a sealing seam, wherein the sealing seam joins at least an outer edge portion of the sealing element with an edge portion of stem-like protrusion of the body arranged surrounding the proximal tip. The sealing seam may be manufactured by a heat sealing process. The sealing seam enables a reliable sealing on the one hand and, on the other hand, a removal of the sealing element from the body may be performed with little effort. Alternatively, the sealing element may be adhesively bonded to the needle cap.

In an exemplary embodiment, the needle assembly includes a deflector element for guiding the sealing element to the outside of the body during removal. The deflector element deflects the sealing element in a manner that it can be removed from the body with less friction. For example, the deflector element is designed as a deflection pulley having a rotating axis that is perpendicular to a longitudinal axis of the needle assembly, whereby the removal movement of the sealing element is facilitated by the rotating deflection pulley. Alternatively, the deflector element may be designed as a polished surface over which the sealing element slides during removal. At least, the design of the deflector element depends on the friction coefficient and stiffness of the sealing element material.

The deflector may define the two sections of the sealing element by dividing the sealing element into two sections. Thus, a grip area of the sealing element can be lead to the outside of the body in the direction of the needle cap enabling a mechanical coupling of both components.

According to this embodiment of the needle assembly including the deflector element, the second section may be arranged outside the body and extending parallel to the longitudinal axis in a distal direction. The two sections of the sealing element are divided by the deflector element that deflects the sealing element in the direction of the needle cap. Thus, a grip area of the sealing element can be lead to the outside of the body in the direction of the needle cap enabling a mechanical coupling of both components.

The present disclosure further provides a medicament delivery device that includes a needle assembly as it is described before. The medicament delivery device is suitable for use as a pen-type device with an automatic needle insertion and/or an automatic medicament delivery.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given herein below and the accompanying drawings which are given by way of illustration only, and thus, are not limitative of the present disclosure, and wherein.

Corresponding parts are marked with the same reference symbols in all figures.

DETAILED DESCRIPTION

In the present application, when the term "proximal section/end" is used, this refers to the section/end of the medicament delivery device M, or the sections/ends of the components thereof, which during use of the medicament delivery device M is located the furthest away from the medicament delivery site of the patient. Correspondingly, when the term "distal section/end" is used, this refers to the section/end of the medicament delivery device M, or the sections/ends of the components thereof, which during use of the medicament delivery device M is located closest to the medicament delivery site of the patient.

By way of illustration, a Cartesian coordinate system with the coordinates x, y and z is illustrated in FIGS. 1 to 5.

Figure 1:
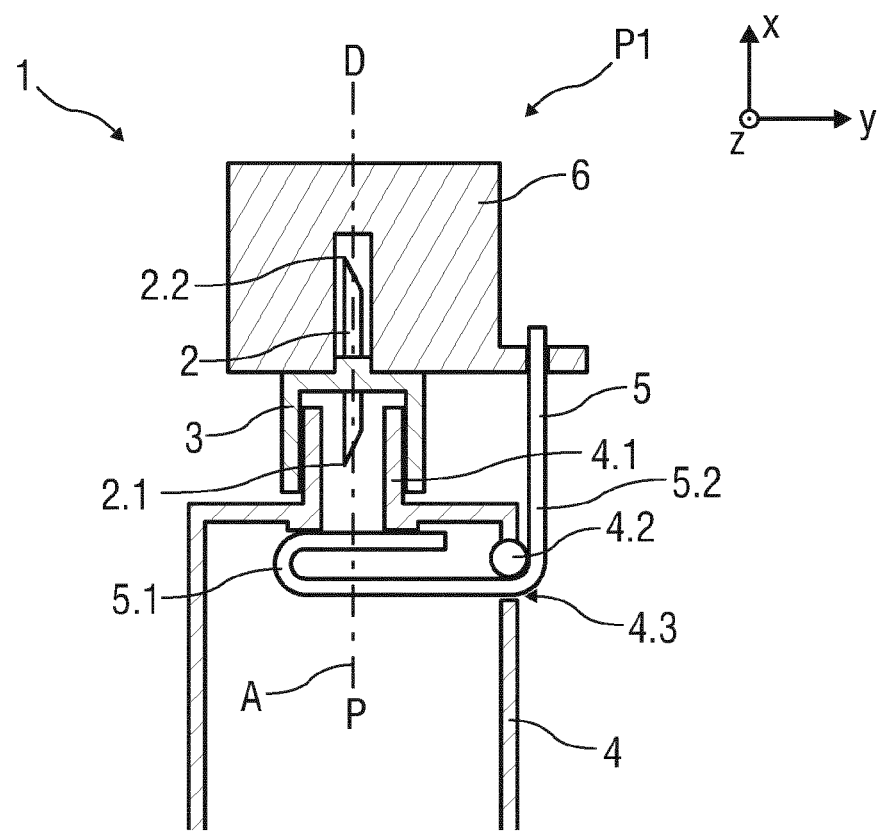
FIG. 1 is a schematic longitudinal section of an exemplary embodiment of a needle assembly in an initial position.
Figure 6:
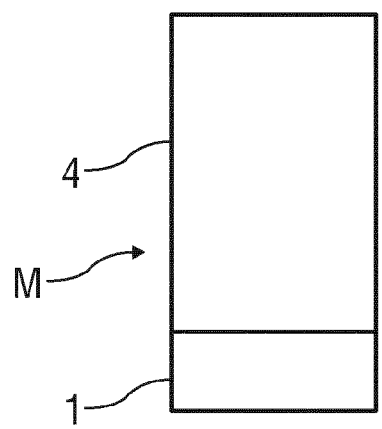

FIG. 1 shows a schematic longitudinal section of an exemplary embodiment of a needle assembly 1 for medicament delivery device M illustrated in FIG. 6, whereby the needle assembly 1 is in an initial position P1.

In the context of the present application, the initial position P1 of the needle assembly 1 is a position in which the needle assembly 1 is substantially hermetically sealed against an outer influences, e.g. contamination, and would be presented to the user before starting an injection process.

The needle assembly 1 includes a longitudinal axis A extending in an x-direction, a hollow double ended needle 2 including a channel for guiding a medicament from a medicament cartridge (not shown) to a patient's site, a needle hub 3, a body 4, a sealing element 5 and a needle cap 6.

The needle 2 is held by the needle hub 3 and includes a proximal tip 2.1 and a distal tip 2.2, wherein the proximal tip 2.1 is sharp or, alternatively blunt. The distal tip 2.2 is directed outside the needle hub 3 in a distal direction D, wherein the proximal tip 2.1 is directed inside the needle hub 3 in a proximal direction P distally spaced from a not shown cartridge of the medicament delivery device M containing a medicament. Thus, the needle 2 is not in fluid communication with the medicament before the beginning of an injection process.

The needle hub 3 is designed as a hollow cylinder that is mechanically coupled to the body 4 by threads, bayonet fit, snap-fit arrangement, friction-fit arrangement, etc. Alternatively, the needle hub 3 and the body 4 are designed as one piece.

The body 4 is designed equally as a hollow cylinder, whereby the present embodiment shows only a part of the body 4 including a compartment 4.1. The compartment 4.1 engages the needle hub 3 and is designed as a hollow stem-like protrusion arranged on a distal end of the body 4 that surrounds the proximal tip 2.1. The body 4 may be a part of the medicament delivery device M holding the medicament cartridge. Hereby, the medicament cartridge is arranged proximally behind the proximal tip 2.1 and the sealing element 5. Alternatively, the body 4 may include a coupling component for coupling the needle assembly 1 with the medicament delivery device M.

The body 4 further includes a deflector element 4.2 that is arranged within a lateral surface of the body 4. Alternatively, the deflector element 4.2 is arranged within a distal surface of the body 4.

In the present embodiment, the deflector element 4.2 is designed as a deflection pulley including a rotational axis that extends parallel to the z-direction. Thus, the deflector element 4.2 deflects the sealing element 5 from an alignment in the y-direction towards an alignment in the x-direction.

The sealing element 5 is guided out laterally of the body 4 through an opening 4.3 arranged in a lateral surface of the body 4. The opening 4.3 corresponds with the dimensions of the sealing element 5. Alternatively, the opening 4.3 is designed with larger dimensions than a width and a thickness of the sealing element 5.

In a not shown alternative embodiment, the deflector element 4.2 is designed as a not rotatable, polished surface over which the sealing element 5 can slide by removal of the sealing element 5 from the body 4. Furthermore, the body 4 may not include a deflector element 4.2 and only include the opening 4.3, through which the sealing element 5 is guided. The design of the deflector element 4.2 or the necessity for arranging a deflector element 4.2 depends on a design of the sealing element 5, in particular on a friction coefficient and a stiffness of a sealing element 5 material.

The sealing element 5 is designed as a foil made from a flexible material, e.g. from plastics. According to the present embodiment of FIG. 1, the sealing element 5 can be divided in two sections 5.1, 5.2, wherein one section 5.1 is mechanically coupled to the body 4 and another section 5.2 is coupled to the needle cap 6.

A free end of the one section 5.1 is arranged covering an open proximal end of the compartment 4.1. For example, an outer edge portion of the free end of the sealing element 5 is connected to an edge portion of the open proximal end of the compartment 4.1 by a seam line that may be generated by a heat sealing process. Alternatively, the sealing element 5 may be coupled to the body 4 by other adhesive bonds suitable for releasing the coupling of both components with little effort.

The one section 5.1 is folded about an angle of 180 degrees so that the open proximal end of the compartment 4.1 is covered by two layers of the sealing element 5 spaced from each other in a proximal direction P. The force required to remove the sealing element 5 is thus reduced, because by removing of the sealing element 5, the force acts not on the entire sealing seam but rather on a section of the sealing seam.

A distance between the two layers corresponds with a dimension of the deflector element 4.2 in the x-direction. The other section 5.2 is arranged outside the body 4 and extends parallel to the longitudinal axis A in a distal direction D.

The sealing element 5 may be divided in the two sections 5.1, 5.2 by the deflector element 4.2 that guides the sealing element 5 in an angle of 90 degrees in the direction of the needle cap 6 so that the one section 5.1 is arranged perpendicular to the other section 5.2. In the area of the right angle, the sealing element 5 is guided through the opening 4.3 outside the body 4.

A free end of the other section 5.2 is mechanically coupled with the needle cap 6, for example by adhesive bonding to generate a solid coupling between the sealing element 5 and the needle cap 6.

As described before, the sealing element 5 may be guided outside the body 4 without a deflector element 4.2, whereby a grip area for removing the sealing element 5 by a user can be arranged on any position outside the body 4 accessible for the user. Thereby, the grip area is formed by the free outside end of the sealing element 5 that may include a manageable removal aid for easily gripping the sealing element 5. In this case, the sealing element 5 may be not mechanically coupled to the needle cap 6.

Figure 2:
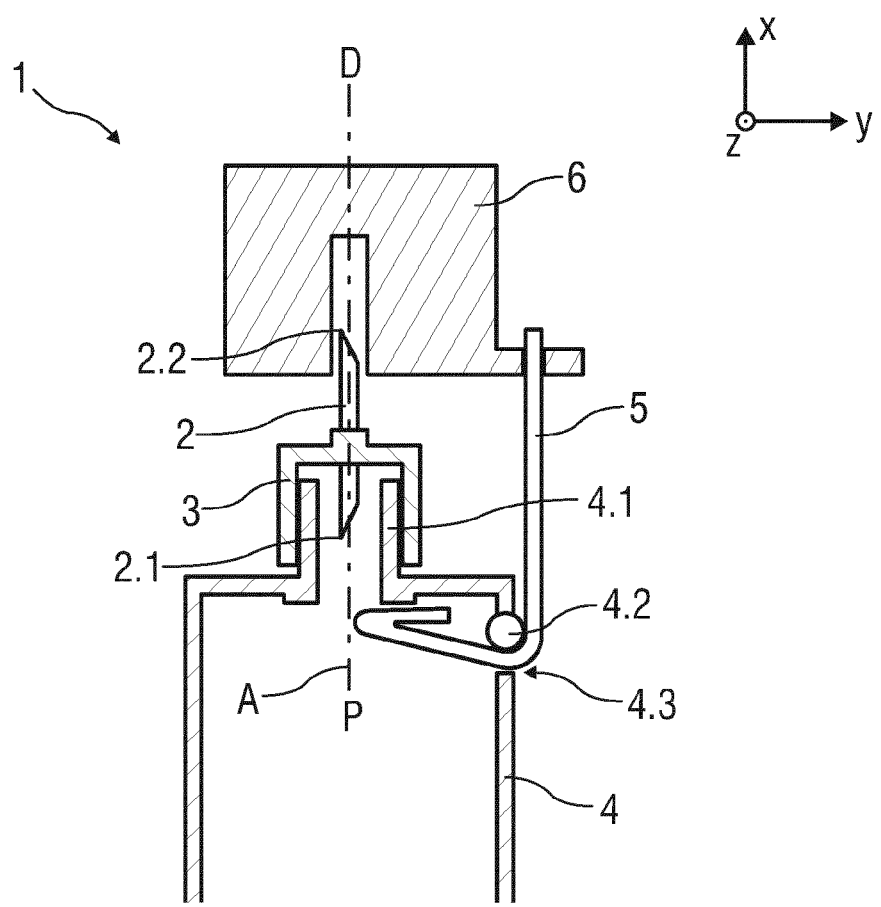
FIG. 2 is a schematic longitudinal section of the needle assembly during removal of a needle cap.
Figure 3:
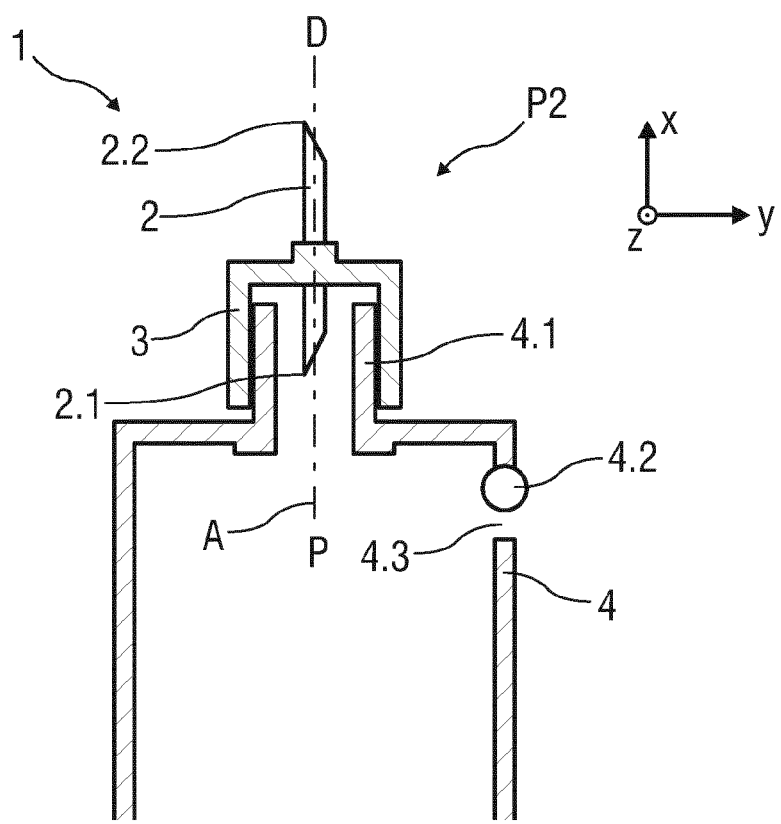
FIG. 3 is a schematic longitudinal section of the needle assembly in a final position.

FIGS. 2 and 3 show the needle assembly 1 in a schematic longitudinal section respectively, wherein FIG. 2 shows the needle assembly 1 during removal of the needle cap 6 and the sealing element 5 and FIG. 3 shows the needle assembly 1 in a final position P2 without the needle cap 6 and the sealing element 5.

For removal of the needle cap 6 and the sealing element 5, the user grips the needle cap 6 and removes it from the needle assembly 1. Because the needle cap 6 and the sealing element 5 are mechanically coupled to each other, the sealing element 5 will be removed at the same time. Thereby, the mechanical coupling of the sealing element 5 and the body 4 will be released and the deflector element 4.2 rotates, thus supporting the movement of the sealing element 5. In case of an absence of the deflector element 4.2 and a non-coupling of the sealing element 5 and the needle cap 6, the sealing element 5 is removable separately from the needle assembly 1 by gripping a free end of the sealing element 5 and pulling off the sealing element 5 from the needle assembly 1.

After removal of the needle cap 6 and the sealing element 5, the needle assembly 1 is in the final position P2 as it is shown in FIG. 3. The proximal and distal tip 2.1, 2.2 are unsealed, wherein the proximal tip 2.1 is ready for piercing the cartridge and subsequently, the medicament delivery device M is ready for starting an injection process.

Figure 4:
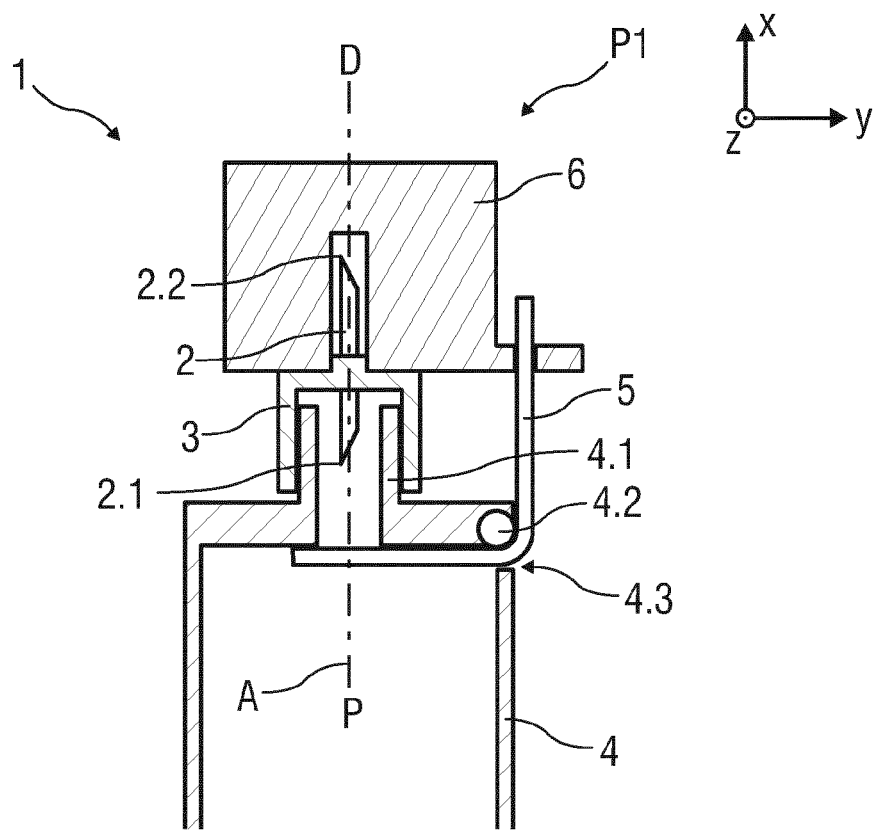
FIG. 4 is a schematic longitudinal section of another exemplary embodiment of the needle assembly in an initial position.

FIG. 4 shows a schematic longitudinal section of another exemplary embodiment of a needle assembly 1, whereby the needle assembly 1 is in the initial position P1.

Here, the proximal tip 2.1 is covered by only one layer of the sealing element 5. The opening 4.3 and the deflector element 4.2 are arranged further distally on the lateral surface of the body 4 compared to the opening 4.3 and the deflector element 4.2 in the exemplary embodiment shown in the FIGS. 1 to 3.

The removal of the sealing element 5 will be performed as it is described in the previously exemplary embodiment.

Figure 5:
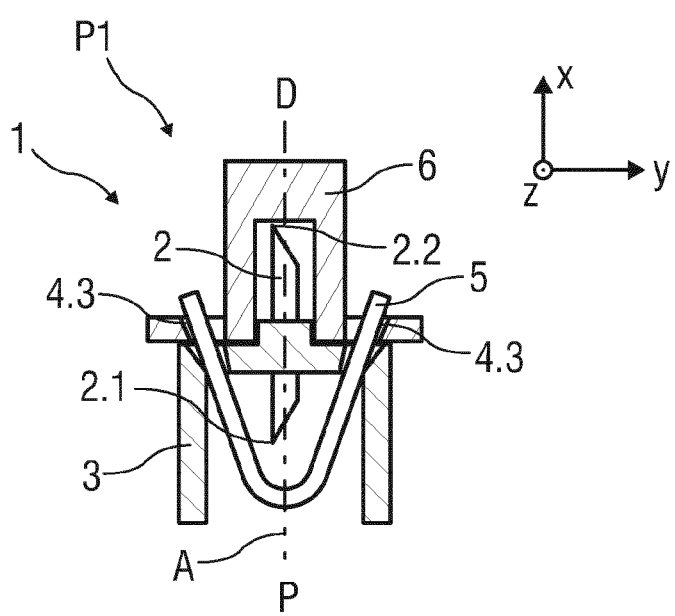
FIG. 5 is a schematic longitudinal section of a further exemplary embodiment of the needle assembly in an initial position and FIG. 6 is a schematic view of a simplified embodiment of a medicament delivery device.

FIG. 5 shows a schematic longitudinal section of a further exemplary embodiment of a needle assembly 1, whereby the needle assembly 1 is in the initial position P1.

The body 4 includes two openings 4.3 that are arranged on a distal surface of the body 4. Both free ends of the sealing element 5 are arranged through the openings 4.3. The sealing element 5 is furthermore coupled to the needle cap 6, wherein the free ends of the sealing element 5 are arranged through corresponding openings on the needle cap 6. One or more of the free ends of the sealing element 5 may be coupled to the needle cap 6. The sealing element 5 is removable by gripping one of the free ends and pulling out the sealing element 5.

FIG. 6 schematically shows a simplified embodiment of a medicament delivery device M including a needle assembly 1 as described above, whereby the body 4 is part of the medicament delivery device M.

The medicament delivery device M may be provided with manual needle insertion and manual medicament delivery. Likewise, the medicament delivery device M could be provided with automatic needle insertion and/or automatic medicament delivery in order to adjust the injection force.

The term "drug" or "medicament", as used herein, means a pharmaceutical formulation containing at least one pharmaceutically active compound.

In some instances, the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound.

In some instances, the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In some instances, the pharmaceutically active compound includes at least one peptide for the treatment and/or prophylaxis of diabetes mellitus or complications associated with diabetes mellitus such as diabetic retinopathy.

In some instances, the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin;

Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two μ sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 needle assembly
2 needle
2.1 proximal tip
2.2 distal tip
3 needle hub
4 body
4.1 compartment
4.2 deflector element
4.3 opening
5 sealing element
5.1 one section
5.2 other section
6 needle cap
M medicament delivery device

The invention claimed is:

1. A needle assembly adapted to couple with a medicament delivery device, the needle assembly comprising:
a needle having a proximal tip and a distal tip;
a needle hub coupled to the needle;
a body adapted to engage the needle hub, wherein the body comprises a compartment that surrounds the proximal tip of the needle;
a removable needle cap adapted to cover the distal tip; and
a removable sealing element adapted to seal an open proximal end of the compartment of the body in such a manner that the proximal tip is housed in a sealed environment before use of the needle, wherein the removable sealing element is coupled to the needle cap such that the removable sealing element is removable from the compartment of the body when the needle cap is removed from the distal tip.

2. The needle assembly according to claim 1, wherein the removable sealing element is movably coupled to the needle cap such that the removable sealing element is removable from the compartment when the needle cap is removed from the distal tip.

3. The needle assembly according to claim 1, wherein the removable sealing element comprises two sections, wherein a first section of the two sections is coupled to the compartment and a second section of the two sections is coupled to the needle cap.

4. The needle assembly according to claim 3, wherein the two sections are arranged perpendicular to each other.

5. The needle assembly according to claim 3, wherein the first section, which is coupled to the compartment, is folded such that the proximal tip is covered by two layers of the removable sealing element.

6. The needle assembly according to claim 3, wherein the second section, which is coupled to the needle cap, is arranged outside of the body and extends parallel to a longitudinal axis of the needle assembly in a distal direction.

7. The needle assembly according to claim 1, wherein the removable sealing element is configured to be guided out of the body through at least one opening of the body when the needle cap is removed from the distal tip.

8. The needle assembly according to claim 7, wherein the at least one opening is arranged in a lateral surface of the body.

9. The needle assembly according to claim 7, wherein the at least one opening is arranged in a distal surface of the body.

10. The needle assembly according to claim 1, wherein the removable sealing element includes a flexible foil.

11. The needle assembly according to claim 1, wherein the removable sealing element is connected to the body by a sealing seam, wherein the sealing seam joins at least an outer edge portion of the removable sealing element with an edge portion of a stem-like protrusion of the body surrounding the proximal tip.

12. The needle assembly according to claim 1, wherein the body comprises a deflector element adapted to guide the removable sealing element to the outside of the body during removal.

13. The needle assembly according to claim 12, wherein the deflector element includes a deflection pulley having a rotating axis that is perpendicular to a longitudinal axis of the needle assembly.

14. The needle assembly according to claim 12, wherein the deflector element includes a polished surface, and the removable sealing element is configured to slide over the polished surface during removal.

15. A medicament delivery device comprising a needle assembly, the needle assembly comprising:
   a needle having a proximal tip and a distal tip;
   a needle hub coupled to the needle;
   a body adapted to engage the needle hub, wherein the body comprises a compartment that surrounds the proximal tip of the needle;
   a removable needle cap adapted to cover the distal tip; and
   a removable sealing element adapted to seal an open proximal end of the compartment of the body including the proximal tip in such a manner that the proximal tip is housed in a sealed environment before use of the needle, wherein the removable sealing element is coupled to the needle cap such that the removable sealing element is removable from the compartment of the body when the needle cap is removed from the distal tip.

16. The medicament delivery device according to claim 15, wherein the removable sealing element comprises two sections, wherein a first section of the two sections is coupled to the compartment and a second section of the two sections is coupled to the needle cap.

17. The medicament delivery device according to claim 16, wherein the first section, which is coupled to the compartment, is folded such that the proximal tip is covered by two layers of the removable sealing element.

18. The medicament delivery device according to claim 16, wherein the second section, which is coupled to the needle cap, is arranged outside of the body and extends parallel to a longitudinal axis of the needle assembly in a distal direction.

19. The medicament delivery device according to claim 15, wherein the removable sealing element is configured to be guided out of the body through at least one opening of the body when the needle cap is removed from the distal tip.

20. The medicament delivery device according to claim 15, wherein the body comprises a deflector element adapted to guide the removable sealing element to the outside of the body during removal.

* * * * *